United States Patent [19]

Cobb

[11] Patent Number: 4,695,671

[45] Date of Patent: Sep. 22, 1987

[54] TETRAMETHYLTETRAHYDRONAPHTHALENE PURIFICATION PROCESS

[75] Inventor: Raymond L. Cobb, Bartlesville, Okla.

[73] Assignee: Phillips Petroleum Company, Bartlesville, Okla.

[21] Appl. No.: 902,786

[22] Filed: Sep. 2, 1986

[51] Int. Cl.$^4$ .............................................. C07C 15/20
[52] U.S. Cl. ..................................... 585/858; 585/425; 208/50
[58] Field of Search ............... 585/858, 811, 803, 469, 585/425

[56] References Cited

U.S. PATENT DOCUMENTS

| | | | |
|---|---|---|---|
| 2,780,662 | 2/1957 | Wilson | 585/858 X |
| 2,875,257 | 2/1959 | Thompson | 585/858 |
| 2,955,144 | 10/1960 | Sisco et al. | 585/858 X |
| 3,311,669 | 3/1967 | Bushiok | 585/425 |
| 3,412,168 | 11/1968 | Masciantonio | 585/858 X |
| 3,856,875 | 12/1974 | Wood et al. | 305/425 X |

FOREIGN PATENT DOCUMENTS

| | | | |
|---|---|---|---|
| 794705 | 5/1958 | United Kingdom | 585/858 |
| 642281 | 1/1979 | U.S.S.R. | 585/425 |

*Primary Examiner*—Andrew H. Metz
*Assistant Examiner*—Glenn Caldarola
*Attorney, Agent, or Firm*—Laney, Dougherty, Hessin & Beavers

[57] ABSTRACT

An improved process for the removal of by-product amounts of undesirable aromatic hydrocarbon compounds from a mixture comprised of such compounds and predominantly tetramethyltetrahydronaphthalene is provided. In accordance with the process the mixture is contacted with a concentrated sulfuric acid solution whereby the undesirable aromatic hydrocarbons are dissolved therein and the acid phase containing said hydrocarbons is removed from the mixture.

12 Claims, No Drawings

TETRAMETHYLTETRAHYDRONAPHTHALENE PURIFICATION PROCESS

BACKGROUND OF THE INVENTION

1. Field of the Invention

The present invention relates to a tetramethyltetrahydronaphthalene purification process, and more particularly, to a process for the removal of by-products from a tetramethyltetrahydronaphthalene product mixture.

2. Description of the Prior Art 1,1,4,4-tetramethyl-1,2,3,4-tetrahydronaphthalene (TMT) can be prepared by first converting commercial 2,5-dimethyl-2,5-hexanediol to 2,5-dichloro-2,5-dimethylhexane by reaction with hydrogen chloride. The 2,5-dichloro-2,5-dimethylhexane is then reacted with excess benzene in the presence of aluminum chloride to yield TMT and a bis cyclialkyl product. Upon prolonged contact with the catalyst and benzene, the bis cyclialkyl product is also converted to TMT. The reaction mixture can be purified to some extent by distillation.

While the foregoing process for producing TMT can result in distilled yields in the range of from about 70 to about 75 mole percent TMT based on the diol starting material, the distilled reaction mixture contains, among other by-products, undesirable aromatic hydrocarbon compounds.

TMT is particularly useful and has achieved favor as an intermediate to a number of perfume fragrances. However, if the TMT product includes by-product amounts or aromatic hydrocarbon compounds, particularly dihydronaphthalenes and indenes, as do both the crude and distilled reaction product mixtures produced as described above, it is generally unacceptable as an intermediate for use by the perfume industry.

Thus, there is a need for a process for producing a purified TMT mixture which does not include objectionable aromatic hydrocarbon compounds.

SUMMARY OF THE INVENTION

The present invention relates to a process for the removal of by-product amounts of undesirable aromatic hydrocarbon compounds from a mixture comprised of such compounds and predominantly tetramethyltetrahydronaphthalene. The process is comprised of contacting the mixture with a concentrated sulfuric acid solution containing in the range of from about 90% to about 100% by weight sulfuric acid in an amount sufficient to cause the dissolution of the undesirable aromatic hydrocarbon compounds and separating the resulting acid phase containing the aromatics from the mixture.

The process of this invention is particularly suitable for the purification of tetramethyltetrahydronaphthalene containing by-product amounts of dihydronaphthalenes and indenes, and the complete removal of such aromatic hydrocarbon compounds can be effected by the process.

Thus, it is a general object of the present invention to provide a tetramethyltetrahydronaphthalene purification process.

A further object of the present invention is the provision of a process for the removal of by-product amounts of undesirable aromatic hydrocarbon compounds, and particularly, dihydronaphthalenes and indenes, from a reaction mixture containing tetramethyltetrhydronaphthalene and by-product amounts of such aromatic hydrocarbon compounds.

Other and further objects, features and advantages of the present invention will be readily apparent to those skilled in the art upon a reading of the description of preferred embodiments which follows.

DESCRIPTION OF PREFERRED EMBODIMENTS

The preparation of tetramethyltetrahydronaphthalene (TMT) utilizing 2,5-dichloro-2,5-dimethylhexane and benzene starting materials in the presence of aluminum chloride has been utilized heretofore. The 2,5-dichloro-2,5-dimethylhexane can be prepared from commercially available 2,5-dimethyl-2,5-hexanediol by treatment of the diol with hydrogen chloride. The dichlorodimethylhexane produced is reacted with benzene in the presence of aluminum chloride to yield TMT and a bis cyclialkyl product. Upon prolonged contact with benzene and the aluminum chloride catalyst, the bis cyclialkyl product is also converted to TMT.

By-products including, among others, aromatic hydrocarbon compounds are produced in the reaction. Upon distillation of the reaction mixture, a number of the by-products are removed. However, the distillate still contains undesirable by-product amounts of aromatic hydrocarbon compounds including dihydronaphthalenes and indenes. As a result of the presence of such compounds in the distilled reaction mixture of TMT, the mixture does not meet required product specifications for use as an intermediate to a number of fragrances produced in the perfume industry.

By the present invention a process for the purification of the crude reaction mixture obtained as described above is provided. The process removes by-product amounts of undesirable aromatic hydrocarbon compounds from the predominantly TMT reaction mixture, specifically by-product amounts of dihydronaphthalenes and indenes. The proces basically comprises contacting the crude or distilled reaction mixture comprised of by-product amounts of undesirable aromatic hydrocarbon compounds and predominantly tetramethyltetrahydronaphthalene with a concentrated sulfuric acid solution whereby the aromatic hydrocarbon compounds are dissolved therein followed by the separation of the acid phase containing the aromatic hydrocarbon compounds from the mixture. The concentrated sulfuric acid selectively reacts with dihydronaphthalenes, indenes, and other aromatic hydrocarbon compounds whereby they are dissolved and removed, but does not appreciably react with the tetramethyltetrahydronaphthalene in the mixture.

The sulfuric acid solutions useful in accordance with the present invention are concentrated sulfuric acid solutions containing in the range of from about 90% to about 100% by weight sulfuric acid, preferably the nominally 96% to 98% by weight commercially available such solutions. The concentrated sulfuric acid solution used is mixed with the reaction mixture to be purified in an amount sufficient to cause the dissolution of the aforesaid undesirable aromatic hydrocarbon compounds. Generally, the concentrated sulfuric acid solution is mixed with the reaction mixture in an amount in the range of from about 2% to about 20% by volume of reaction mixture. A 96% by weight sulfuric acid solution is most preferred, and it is preferably mixed with the reaction mixture in an amount in the range of from about 5% to about 10% by volume of the mixture.

The undesirable aromatic hydrocarbon compounds are dissolved in the sulfuric acid shortly after mixing. The acid phase containing the aromatic compounds is removed using conventional techniques whereby the remaining mixture is substantially void of such aromatic hydrocarbon compounds, particularly, dihydronaphthalenes and indenes.

While the process can be carried out at room temperatures, the rate of dissolution of the aromatic hydrocarbons is increased at higher temperatures, e.g., 40° to 45° C.

In order to further illustrate and facilitate a clear understanding of the process of the present invention, the following example is given.

EXAMPLE

Crude and distilled reaction product mixtures comprised of tetramethyltetrahydronaphthalene and various by-products including undesirable aromatic hydrocarbon compounds are prepared as follows. A mixture of 1250 grams (8.56 moles) of 2,5-dimethyl-2,5-hexanediol and 500 milliliters of an aqueous hydrochloric acid-zinc chloride catalyst solution in 1500 milliliters of benzene is treated with gaseous hydrogen chloride for about 7 to 8 hours, at which time gas-liquid chromatography (GLC) analysis shows only 2 to 3% of the initially formed 2,2,5,5-tetramethyltetrahydrofuran remaining. The benzene layer is separated, washed with water and heated under aspirator pressure (steam bath) until there is no water in the benzene overhead. The resulting "dried" solution is added over a 60 minute period to a stirred suspension of 305 grams of anhydrous aluminum chloride and 5 liters of benzene. During the addition the temperature rises to 34° C. with the evolution of hydrogen chloride. An additional 5 liters of benzene are added, and the mixture is stirred at about 43° C. to 45° C. for 8 hours with periodic removal of samples for GLC analysis. At the end of 8 hours, GLC analysis shows tetramethyltetrahydronaphthalene and a bi cyclialkyl product present at 88 and 8 volume percents, respectively. To the stirred reaction mixture, about 600 milliliters of water are slowly added, followed by another liter which is added rapidly. The recovered benzene product phase is washed with water and then distilled through a short Vigreux section to a pot temperature of about 165° C. to remove benzene and lights, leaving residual oil containing about 70–75% TMT.

The reaction product mixtures before and after distillation are analyzed by mass/GLC, and samples thereof are treated with various reagents to determine their affect on by-product amounts of undesirable aromatic hydrocarbon compounds contained in the mixtures, particularly dihydronaphthalenes and indenes. The results of these tests are given in Table I below.

TABLE I
PRETREATMENT OF PRODUCT MIXTURES FOR BY-PRODUCT REMOVAL

| Capillary GLC Retention Time, Minutes | Products Identified By Mass/GLC | Product Mixture Before Treatment, Vol % | | PRODUCT MIXTURE AFTER TREATMENT WITH VARIOUS REAGENTS, VOL % Distilled Product Mixture | | |
|---|---|---|---|---|---|---|
| | | Distilled | Crude | Concentrated Sulfuric Acid (96% by wt.) | Tungsto-Phosphoric Acid | Silica Aluminia |
| 9.96 | | 0.47 | | 0.39 | 0.42 | |
| 10.07 | | 1.03 | 0.24 | 1.09 | 1.02 | 0.91 |
| 10.12 | | 2.37 | | 2.47 | 2.34 | 2.21 |
| 10.39 | dihydronaph- | 18.29 (combined 10.39 and 10.45 minutes) | 4.13 (combined 10.39 and 10.45 minutes) | 8.31 | 16.89 (combined 10.39 and 10.45 minutes) | 5.42 |
| 10.45 | thalenes and indenes | | | 0 | | 12.30 |
| 10.66 | | 8.54 | 1.26 | 10.13 | 8.75 | 8.19 |
| 10.85 | dihydronaphthalenes and indenes | 1.24 | | 0 | 1.33 | 0.91 |
| 11.00 | tetramethyltetrahydronaphthalene | 66.95 | 82.04 | 75.47 | 67.79 | 68.36 |
| 11.15 | | 1.15 | 2.13 | 0.86 | 1.47 | 1.71 |
| 11.23 | | | 1.24 | | | |
| 11.30 | | | 0.52 | | | |
| 11.36 | | | 0.84 | | | |
| 11.46 | | | 1.14 | | | |
| 12.26 | | | 1.81 | 1.28 | | |
| 12.68 | | | 0.38 | | | |
| 17.46 | | | 1.46 | | | |
| 19.12 | | | 0.68 | | | |

| Capillary GLC Retention Time, Minutes | PRODUCT MIXTURE AFTER TREATMENT WITH VARIOUS REAGENTS, VOL % | | | |
|---|---|---|---|---|
| | Distilled Product Mixture | | Crude Product Mixture | |
| | Gamma Alumina | Silica | Sulfuric Acid (75% by wt.) | Concentrated Sulfuric Acid (96% by wt.) |
| 9.96 | 0.39 | 0.48 | | |
| 10.07 | 0.99 | 1.01 | 0.24 | 0.25 |
| 10.12 | 2.23 | 2.34 | | |
| 10.39 | 18.13 (combined 10.39 and 10.45 minutes) | 18.29 (combined 10.39 and 10.45 minutes) | 4.13 (combined 10.39 and 10.45 minutes) | 0.57 |
| 10.45 | | | | 1.08 |
| 10.66 | 8.56 | 8.62 | 1.26 | 2.28 |
| 10.85 | 1.16 | 1.25 | | 0 |

TABLE I-continued
PRETREATMENT OF PRODUCT MIXTURES FOR BY-PRODUCT REMOVAL

| | | | |
|---|---|---|---|
| 11.00 | 67.47 | 66.97 | 82.04 | 88.36 |
| 11.15 | 1.08 | 0.99 | 2.13 | 0.54 |
| 11.23 | | | 1.24 | |
| 11.30 | | | 0.52 | |
| 11.36 | | | 0.84 | 0.68 |
| 11.46 | | | 1.14 | 0.98 |
| 12.26 | | | 1.81 | 0.66 |
| 12.68 | | | 0.38 | 0.29 |
| 17.46 | | | 1.46 | 1.87 |
| 19.12 | | | 0.68 | 0.78 |

From Table I it can be seen that sulfuric acid at a concentration of about 96% by weight effectively removes or reduces dihydronaphthalenes and indenes in TMT reaction mixtures.

From the foregoing description, one skilled in the art can readily ascertain the essential characteristics of this invention, and without departing from the spirit and scope thereof, can make various changes and modifications of the invention to adapt it to various usages and conditions.

What is claimed is:

1. A process for the removal of by-product amounts of aromatic hydrocarbon compounds from a mixture comprised of aid compounds and predominantly tetramethyltetrahydronaphthalene comprising the steps of:
    contacting said mixture with a sulfuric acid solution containing in the range of from about 90% to about 100% by weight sulfuric acid in an amount sufficient to cause the dissolution of said aromatic hydrocarbon compounds; and
    separating the resulting acid phase containing said aromatic hydrocarbon compounds from said mixture.

2. The process of claim 1 wherein said mixture comprised of said undesirable aromatic hydrocarbon compounds and tetramethyltetrahydronaphthalene is produced by reacting dichlorodimethylhexane with benzene in the presence of aluminum chloride catalyst.

3. The process of claim 2 wherein said aromatic hydrocarbon compounds are comprised of dihydronaphthalenes and indenes.

4. The process of claim 2 wherein said amount of said sulfuric acid acid solution contacted with said mixture is in an amount in the range of from about 2% to about 20% by volume of said mixture.

5. The process of claim 2 wherein said sulfuric acid solution contains about 96% by weight sulfuric acid and said mixture is contacted therewith in an amount in the range of from about 5% to about 10% by volume of said mixture.

6. In a process of preparing tetramethyltetrahydronaphthalene wherein dichlorodimethylhexane is reacted with benzene in the presence of aluminum chloride, the improvement wherein byproduct amounts of aromatic hydrocarbons are removed from the reaction mixture produced comprising the steps of:
    combining said reaction mixture with a sulfuric acid solution containing in the range of from about 90% to about 100% by weight sulfuric acid in an amount of from about 2% to about 20% by volume of said reaction mixture so that said aromatic hydrocarbons are caused to be dissolved in said sulfuric acid solution; and
    separating the resulting acid phase containing said undesirable aromatic hydrocarbons from said reaction mixture.

7. The process of claim 6 wherein said aromatic byproducts are comprised of dihydronaphthalenes and indenes.

8. The process of claim 7 wherein said concentrated sulfuric acid solution contains about 96% by weight sulfuric acid.

9. The process of claim 8 wherein said sulfuric acid solution is combined with said reaction mixture in an amount in the range of from about 5% to about 10% by volume of said mixture.

10. The process of claim 9 wherein said reaction mixture is distilled prior to combining said sulfuric acid solution therewith and said sulfuric acid solution is combined with the distillate obtained.

11. The process of claim 10 wherein said process is carried out at a temperature in the range from about room temperature to about 45° C.

12. The process of claim 5 wherein said process is carried out at a temperature in the range of from about room temperature to about 45° C.

* * * * *

UNITED STATES PATENT AND TRADEMARK OFFICE
CERTIFICATE OF CORRECTION

PATENT NO. : 4,695,671
DATED : September 22, 1987
INVENTOR(S) : Raymond L. Cobb

It is certified that error appears in the above-identified patent and that said Letters Patent are hereby corrected as shown below:

Column 5, line 27, change "aid" to --said--.

Signed and Sealed this

Twelfth Day of January, 1988

Attest:

DONALD J. QUIGG

Attesting Officer

Commissioner of Patents and Trademarks